Feb. 27, 1973 W. H. JESSEL, JR., ET AL Plant Pat. 3,313
CHRYSANTHEMUM PLANT
Filed June 15, 1971
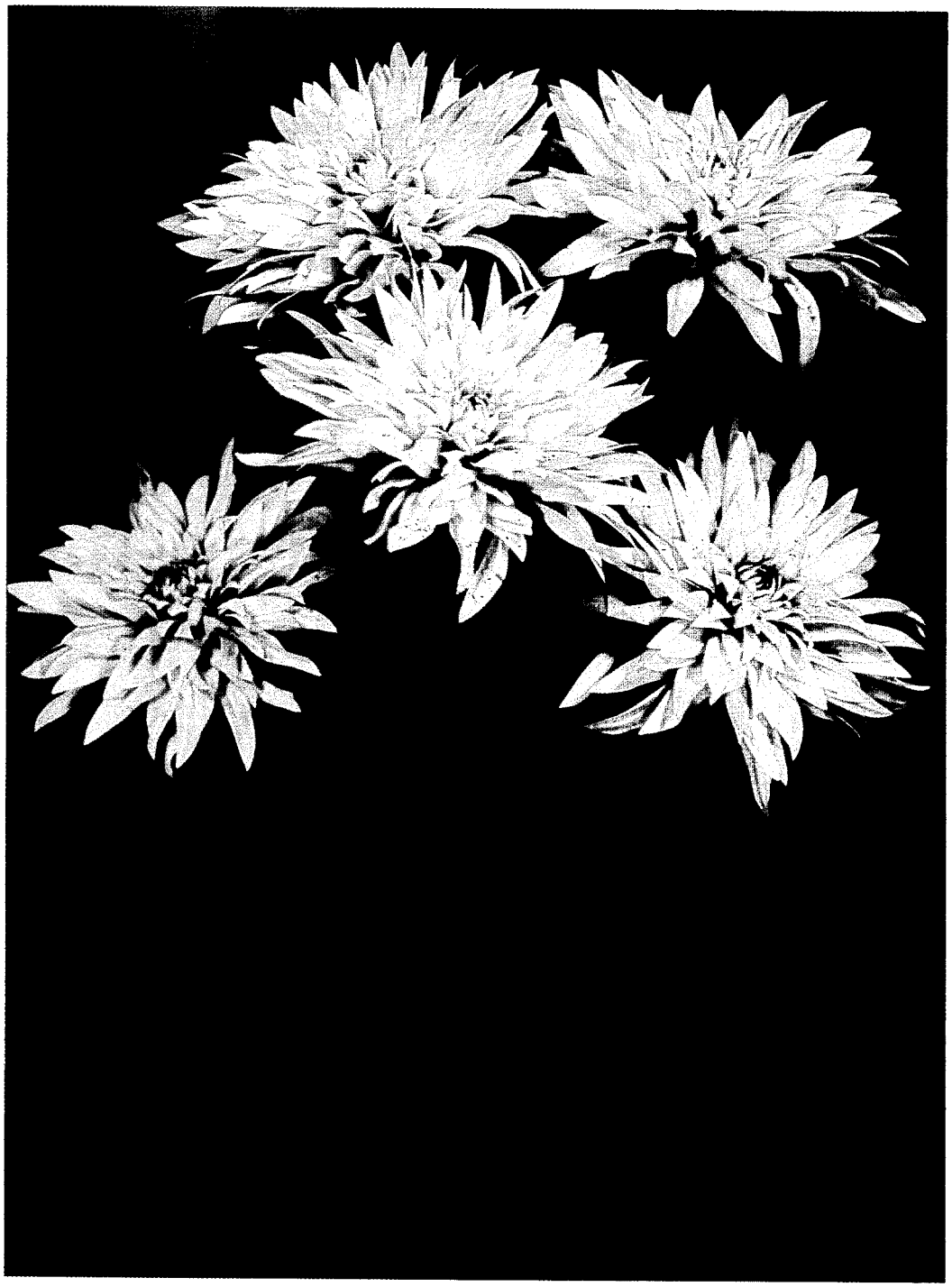
INVENTORS
WALTER H. JESSEL, Jr.,
WILLIAM E. DUFFETT
BY Oberlin, Maky, Donnelly & Renner
ATTORNEYS

United States Patent Office

Plant Pat. 3,313
Patented Feb. 27, 1973

3,313
CHRYSANTHEMUM PLANT

Walter H. Jessel, Jr., Doylestown, and William E. Duffett, Akron, Ohio, assignors to Yoder Brothers, Inc., Barberton, Ohio

Filed June 15, 1971, Ser. No. 153,457
Int. Cl. A01h *5/00*
U.S. Cl. Plt.—80 1 Claim

The present invention comprises a new and distinct cultivar of chrysanthemum plant which is a seedling of parents identified for breeding purposes as #5742–2× 611666–7. Both parents are unpatented and are identified by the above numbers to distinguish the same from other parents in the same breeding program.

The new cultivar is similar in certain respects to Caravelle, the characteristics of which are disclosed and illustrated in our copending application Ser. No. 95,000, filed Dec. 3, 1970, and assigned to Yoder Brothers, Inc., Barberton, Ohio, assignee herein. The new cultivar has the same characteristics as Caravelle of:

(1) A recommended flowering period during winter.
(2) Smooth flower texture.
(3) Deeply indented foliage.

The new cultivar is distinguished from Caravelle by the following characteristics when grown under comparable conditions:

(1) A longer recommended flowering period.
(2) One week earlier response.
(3) Approximately one inch to one-and-a-quarter inches larger flower.
(4) A flatter petal and more decorative, less formal flower form.
(5) A more salmon pink, rather than a lavender pink color, with better color retention.
(6) Approximately 4″ more vigor.
(7) Lighter foliage color.
(8) Foliage more coarse in texture.
(9) More prominent stipules.
(10) Less prominent veins in the leaves.

The new cultivar is also similar in certain respects to the unpatented, commercial cultivar known in the United States as Telstar, the new cultivar having the same characteristics as Telstar of:

(1) Decorative form.
(2) 10 week response.
(3) Period of value.
(4) Vigorous habit.

The new clutivar is distinguished from Telstar by the following characteristics when grown under comparable conditions:

(1) A flower approximately ¾″ smaller at maturity.
(2) Less reflexing of the petals as the flower matures.
(3) More salmon pink coloration.
(4) Approximately 1″ more vigor.
(5) Lighter foliage color.
(6) Smaller foliage.
(7) Smaller stipules.

The new cultivar was selected from the progeny of the designated cross and when asexually reproduced by cuttings at Barberton, Ohio, has been found to retain its distinctive characteristics through successive propagations.

Our new cultivar when grown in the vicinity of Barberton, Ohio, has a response period of approximately 10 weeks, and the following detailed description is based on observations made of the new cultivar in a greenhouse in Barberton, Ohio. The response time, blooming period, color and total vigor may vary significantly with varying environmental conditions such as temperature, day length, and light intensity. Suggested flowering in the northern and western United States is from October through May; in Florida, from December through April.

The accompanying drawing shows the unique characteristics of the new cultivar, the color being as nearly true as possible with color illustrations of this type.

In the following description, color references are made to the Munsell Color Book, 1963 edition, and comparisons are made with the cultivars Caravelle and Telstar. Where values do not appear for one or both of the comparison cultivars, the value or description of the new cultivar applies also to the comparison cultivar or cultivars.

Botanical classification: *Chrysanthemum morifolium*

| | Tally Ho | Caravelle | Telstar |
|---|---|---|---|
| Bloom: | | | |
| Size | 3¾″ | 2½″ | 3¼″. |
| Fully expanded | 4¼″ | 3″ | 5″. |
| Borne | | Clusters on elongated pedicels | |
| Stems | Wiry and strong | Wiry and strong | Strong. |
| Form | | Decorative | |
| Permanence | 10–14 days | 10–12 days | 10–14 days. |
| Color: | | | |
| Center of flower | Light beige, 7.5YR8/4 | Light greenish yellow, 10Y/4 | Pale lavender 5RP9/2. |
| Base of petals | Lavender pink, 2.5RP8/4 | Lavender pink, 10P7/8 to lavender pink, 10P8/6. | Pale lavender 2.5RP9/2 to pale lavender 5RP9/2. |
| Inside of petals | do | do | Do. |
| Reverse of petals | Lavender pink, 5RP8/4 | Pale lavender, 10P9/2 | Very pale lavender 5RP9/1. |
| Tonality from a distance. | Salmon pink | Lavender pink | Light lavender. |
| Discoloration | do | Lavender pink, 10P8/6 | Pale lavender 5RP9/2. |
| Petals: | | | |
| Texture | | Smooth | |
| Appearance and form | Open at base, flat broadens quickly, long and narrow, terminating in a sharp point. | Open at base, broad ridged shallow keel, tapering to a sharp point. | Open at base, broad shallow ridged keel, tapeing to a blunt point. |
| Arrangement | | Composite, whorled on a single receptacle | |
| Persistence | | Resist shatter | |
| Fragrance | | Typical chrysanthemum | |
| Reproductive Organs. | | | |
| Stamen, anthers | 0–5 | 0–10 | None. |
| Pollen | None | None—very scant | Do. |
| Arrangement | | Clustered in center of flower, if present | |
| Styles | Present both ray and disc florets | Present both ray and disc florets | Present ray florets. |
| Length | | Short | |
| Ovaries | | At the base of petal attached to receptacle | |
| Plant: | | | |
| Form | | Herbaceous | |
| Growth | | Upright | |
| Height | Approximately 46″ when grown single stem with five long day weeks, with fifteen week croptime under comparable conditions. | Approximately 42″ when grown single stem with four long day weeks, with fifteen week croptime under comparable conditions. | Approximately 45″ when grow single stem with fifteen week croptime under comparable conditions. |
| Spread | None when grown single stem to slight when pinched. | None when grown single stem to slight when pinched. | None when grown single stem to moderate when pinched. |

| | Tally Ho | Caravelle | Telstar |
|---|---|---|---|
| Foliage: | | | |
| Top side | Green, 7.5GY4/4 | Very dark green, 10GY2/4 | Very dark green, 10GY2/4. |
| Size | 6″ long, 3½″ wide | 5½″ long, 3″ wide | 7½″ long, wide 5″. |
| Quantity | | Numerous | |
| Shape | | Spatulate lobed | |
| Texture | Coarse | Smooth | Smooth |
| Ribs and veins | Prominent | Very prominent | Very prominent. |
| Edge | | Deeply indented | |
| Serration | | Coarse | |
| Under side | Light green, 5GY5/4 | Light green, 7.5GY5/4 | Light green, 7.5GY5/4. |
| Stipules | Prominent base of stem, rudimentary upper portion. | Rudimentary | Very prominent. |

We claim:

1. A new and distinct cultivar of chrysanthemum characterized particularly as to its uniqueness when compared to the cultivar Caravelle by a longer recommended flowering period, one week earlier response, approximately one inch to one-and-a-quarter inches larger flower, a flatter petal and more decorative, less formal flower form, a more salmon pink flower color, with better color retention, approximately 4″ more vigor, lighter color and more coarse foliage, more prominent stipules, and less prominent veins in the leaves; and characterized particularly as to its uniqueness when compared to the cultivar Telstar by a flower approximately ¾″ smaller at maturity, less reflexing of the petals as the flower matures, more salmon pink coloration, approximately 1″ more vigor, foliage which is lighter in color and smaller, and smaller stipules.

No references cited.

ROBERT E. BAGWILL, Primary Examiner